(12) United States Patent
Vitzrabin et al.

(10) Patent No.: US 11,609,570 B2
(45) Date of Patent: Mar. 21, 2023

(54) PROTECTION OF ULTRAVIOLET (UV) LIGHT SOURCE ON MOBILE DEVICE

(71) Applicant: UVD Robots Aps, Odense (DK)

(72) Inventors: Efraim Vitzrabin, Odense (DK); Rune K. Larsen, Odense (DK); John Erland Østergaard, Odense (DK); Jorge Rodriguez, Copenhagen (DK); Thomas Rubaek, Odense (DK)

(73) Assignee: UVD Robots ApS, Odense (DK)

( * ) Notice: Subject to any disclaimer, the term of this patent is extended or adjusted under 35 U.S.C. 154(b) by 304 days.

(21) Appl. No.: 16/836,740

(22) Filed: Mar. 31, 2020

(65) Prior Publication Data
US 2021/0286363 A1    Sep. 16, 2021

(30) Foreign Application Priority Data
Mar. 16, 2020 (EP) ..................... 20163352

(51) Int. Cl.
*G05D 1/02* (2020.01)
*A61L 2/10* (2006.01)
*G05D 1/00* (2006.01)

(52) U.S. Cl.
CPC .............. *G05D 1/0212* (2013.01); *A61L 2/10* (2013.01); *G05D 1/0016* (2013.01);
(Continued)

(58) Field of Classification Search
CPC .. G05D 1/0212; G05D 1/0016; G05D 1/0238; G05D 1/0257; G05D 2201/02;
(Continued)

(56) References Cited

U.S. PATENT DOCUMENTS

| 10,010,633 B2 * | 7/2018 | Trapani ............ A61L 2/10 |
| 2002/0085947 A1 * | 7/2002 | Deal ............... A61L 2/10 |
| | | 422/906 |

(Continued)

FOREIGN PATENT DOCUMENTS

| CN | 104487100 | 4/2015 |
| CN | 208641335 | 3/2019 |

(Continued)

OTHER PUBLICATIONS

Extended European search Report received in App. No. EP20163352.6 dated Sep. 29, 2020, 7 pages.
(Continued)

*Primary Examiner* — Jason Holloway
(74) *Attorney, Agent, or Firm* — Kevin Roddy; Butzel Long

(57) ABSTRACT

Implementations of the disclosed subject matter provide a device of a mobile robot may include a motor to drive a drive system to move the mobile robot in an area, and a light source to output ultraviolet light. The device may include at least one first sensor to determine at least one of an orientation of the mobile robot, a location of the mobile robot, and/or when the light source is within a predetermined distance of an object in the area. The device may include a controller, communicatively coupled to the drive system, the light source, and the at least one first sensor to control the drive system so as to stop or move the mobile robot before the light source is within the predetermined distance of the object based on at least a signal received from the at least one first sensor.

14 Claims, 4 Drawing Sheets

(52) U.S. Cl.
CPC ......... *G05D 1/0238* (2013.01); *G05D 1/0257* (2013.01); *A61L 2202/11* (2013.01); *A61L 2202/14* (2013.01); *A61L 2202/16* (2013.01); *G05D 2201/02* (2013.01)

(58) Field of Classification Search
CPC  G05D 2201/0203; G05D 1/0214; A61L 2/10; A61L 2202/11; A61L 2202/14; A61L 2202/16
See application file for complete search history.

(56) References Cited

U.S. PATENT DOCUMENTS

| | | | | |
|---|---|---|---|---|
| 2008/0056933 | A1* | 3/2008 | Moore | A47L 11/4011 422/4 |
| 2012/0223216 | A1* | 9/2012 | Flaherty | G05D 1/0242 901/1 |
| 2014/0044590 | A1* | 2/2014 | Trapani | G01J 1/429 422/3 |
| 2015/0217012 | A1* | 8/2015 | Garner | A61L 2/24 422/24 |
| 2016/0271803 | A1* | 9/2016 | Stewart | B25J 11/0085 |
| 2016/0296649 | A1* | 10/2016 | Ramanand | A61L 2/28 |
| 2016/0375166 | A1* | 12/2016 | Kreitenberg | A61L 2/24 422/24 |
| 2018/0193502 | A1* | 7/2018 | Ufkes | A61B 90/70 |

FOREIGN PATENT DOCUMENTS

| | | |
|---|---|---|
| CN | 209529745 | 10/2019 |
| WO | 2004082899 A2 | 9/2004 |
| WO | 2019222589 | 11/2019 |

OTHER PUBLICATIONS

Search Report (with translation) and Official Letter received in App. No. TW109108638 dated Dec. 29, 2020, 4 pages.
European Patent Office Communication pursuant to Article 94(3) EPC for App. No. EP20163352.6, dated Apr. 5, 2022, 3 pages.

* cited by examiner

PROTECTION OF ULTRAVIOLET (UV) LIGHT SOURCE ON MOBILE DEVICE

BACKGROUND

Mobile devices, such as mobile robots, can be operated so as to change direction after striking a surface, such as a wall. Some mobile robots can detect humans in a determined path of direction, and change the determined path.

BRIEF SUMMARY

According to an implementation of the disclosed subject matter, a device may be a mobile robot that may include a motor to drive a drive system to move the mobile robot in an area, and a light source to output ultraviolet light. The device may include at least one first sensor to determine at least one of an orientation of the mobile robot, a location of the mobile robot, and/or when the light source is within a predetermined distance of an object in the area. The device may include a controller, communicatively coupled to the drive system, the light source, and the at least one first sensor to control the drive system so as to stop or move the mobile robot before the light source is within the predetermined distance of the object based on at least a signal received from the at least one first sensor.

Additional features, advantages, and implementations of the disclosed subject matter may be set forth or apparent from consideration of the following detailed description, drawings, and claims. Moreover, it is to be understood that both the foregoing summary and the following detailed description are illustrative and are intended to provide further explanation without limiting the scope of the claims.

BRIEF DESCRIPTION OF THE DRAWINGS

The accompanying drawings, which are included to provide a further understanding of the disclosed subject matter, are incorporated in and constitute a part of this specification. The drawings also illustrate implementations of the disclosed subject matter and together with the detailed description serve to explain the principles of implementations of the disclosed subject matter. No attempt is made to show structural details in more detail than may be necessary for a fundamental understanding of the disclosed subject matter and various ways in which it may be practiced.

DETAILED DESCRIPTION

In implementations of the disclosed subject matter, a mobile robot may emit ultraviolet (UV) light from a UV light source. The UV light output by the light source may be used to disinfect an object, at least a portion of a room, a predetermined area, or the like. The mobile robot may be used as part of a regular cleaning cycle of a room, building, or the like, and may prevent and/or reduce the spread of infectious diseases, viruses, bacteria, and other types of harmful organic microorganisms in the environment by breaking down their DNA-structure with UV light. The mobile robot may reduce human error in cleaning an area, room, building, or the like by tracking the location and/or intensity (e.g., optical power of UV light) of light radiated, and determine which areas may need to be radiated and/or cleaned.

The mobile robot may be operated manually, autonomously, and/or may receive control signals to control the movement of the mobile robot with a room, building, area, or the like when operating in a tele-operation mode.

The UV light source of the mobile robot may be protected by one or more sensors disposed on the mobile robot. The sensors may prevent the mobile robot from moving to a location having one or more objects that may damage the UV light source. The one or more sensors may be communicatively coupled to a controller, which may control the movement of the mobile robot based on signals received from the one or more sensors. This differs from traditional mobile robots, which may avoid objects and/or humans to prevent damaging the objects or harming humans. That is, implementations of the disclosed subject matter provide sensors to detect obstacles which may potentially damage the mobile robot, such as its UV light source.

Although a protective shield may be used to at least partially cover and/or enclose the UV light source, the magnitude of the UV light (i.e., the optical power of the UV light) may physically deform the protective shield over time, and/or the protective shield may attenuate the amount of UV light that may radiate a predetermined area, which may be detrimental in preventing the spread of harmful organic microorganisms.

Figure 1:
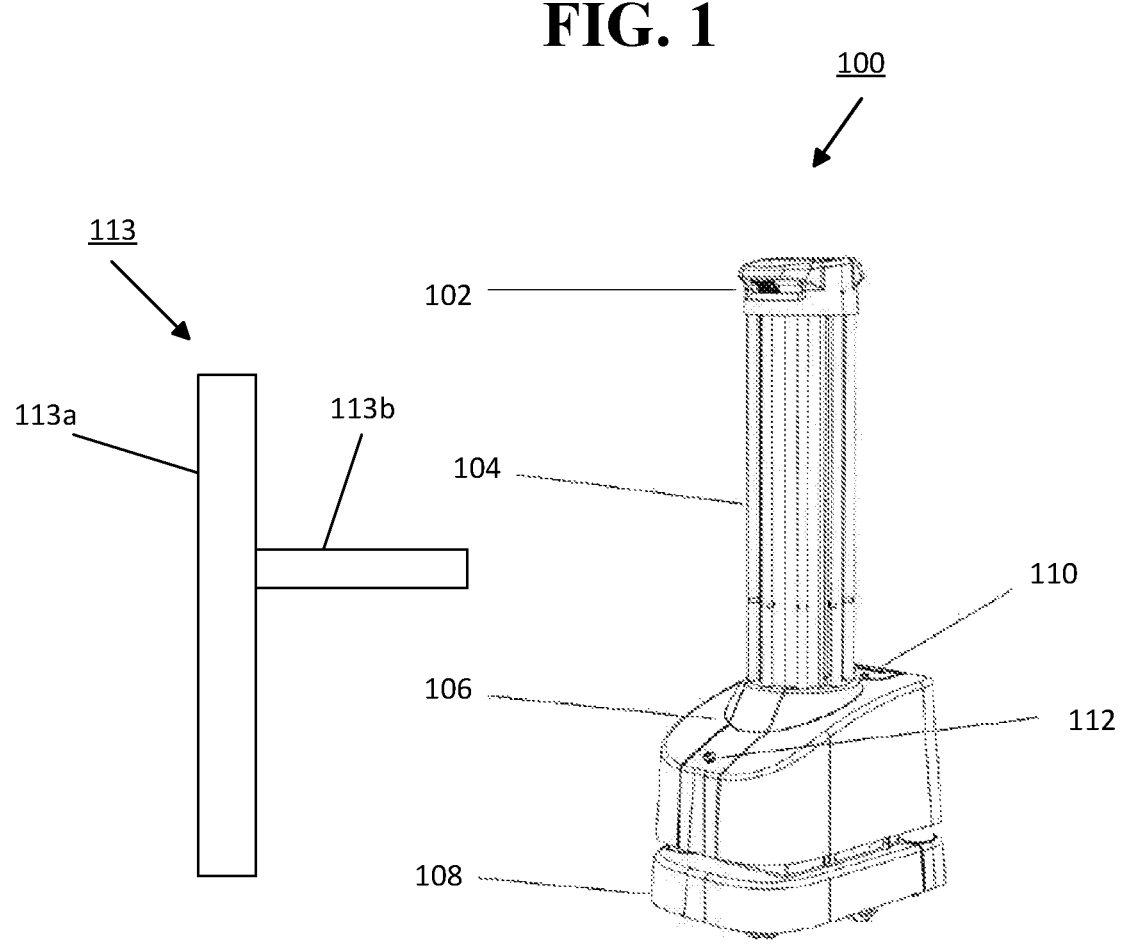
FIGS. 1-3 show a plurality of external views of a mobile robot having sensors to protect an ultraviolet (UV) light source according to implementations of the disclosed subject matter.
Figure 2:
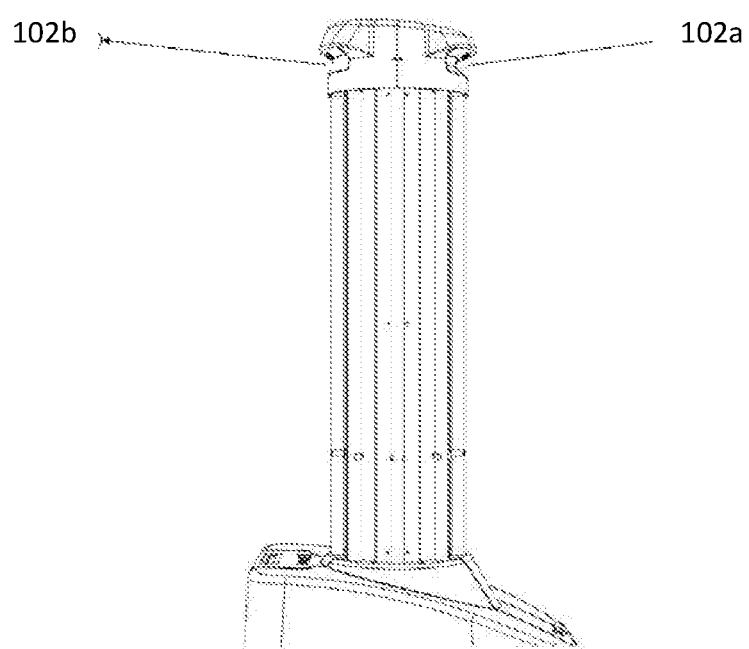
Figure 3:
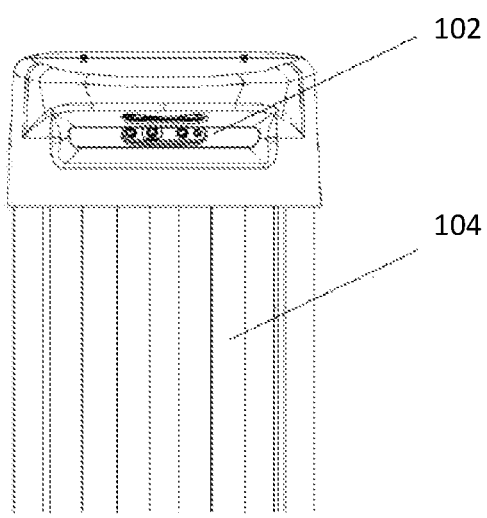

FIGS. 1-3 show a plurality of external views of a mobile robot 100 with sensors to protect an ultraviolet (UV) light source according to implementations of the disclosed subject matter. The mobile robot 100 may include at least a first sensor 102 (shown as sensor 102a and 102b in FIG. 2), a light source 104 to output ultraviolet light, at least a second sensor 106, a drive system 108, a user interface 110, and/or a stop button 112. A controller (e.g., controller 114 shown in FIG. 4 and described below) may be communicatively coupled to the at least one first sensor 102, the light source 104, the at least one second sensor 106, the drive system 108, the user interface 110 and the stop button 112, may control the operations of the mobile robot 100.

The at least one first sensor 102 (including sensors 102a, 102b shown in FIG. 2) may determine at least one of an orientation of the mobile robot 100 (e.g., a direction that a front side and/or a first side of a robot is facing), a location of the mobile robot 100 (e.g., a location of the mobile robot 100 in an area), and/or when the light source 104 is within a predetermined distance of an object 113 (which may include 113a, 113b) in the area. In some implementations, the at least one first sensor 102 may have a field of view of 70 degrees diagonally. The at least one sensor 102 may have a detection distance of 0.2-4 meters. As shown in FIGS. 1-3, the at least one first sensor 102 may be disposed over the light source 104.

The at least one first sensor 102 may include a first side sensor disposed on a first side of the mobile robot 100 and a second side sensor that may be disposed on a second side of the device. For example, as shown in FIG. 2, sensor 102a may be disposed on a first side (e.g., a front side) of the mobile robot 100, and sensor 102b may be disposed on a second side (e.g., a back side) of the mobile robot 100. Although sensors on two sides of the robot are shown in FIG. 2, there may be a plurality of sensors disposed on different sides of the mobile robot 102 to prevent an object from damaging the light source 104. In some implementations, sensor 102a and/or sensor 102b may be disposed over the light source 104.

The light source 104 may be one or more bulbs, one or more lamps, and/or an array of light emitting diodes (LEDs) or organic light emitting diodes (OLEDs) to emit UV light (e.g., light having a wavelength of 10 nm-400 nm). The intensity (i.e., optical power output) may be controlled by the controller 114, which may also turn on or off a portion or all of the devices (e.g., bulbs, lamps, LEDs, OLEDs) of the light source 104.

Figure 4:
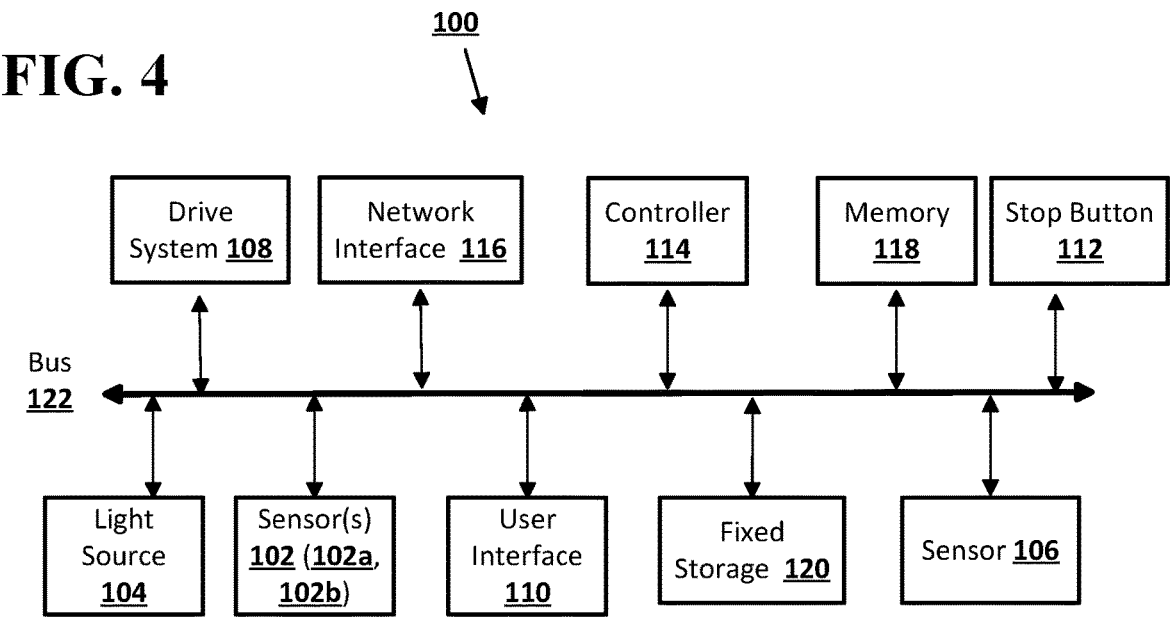
FIG. 4 shows an example configuration of the mobile robot of FIGS. 1-3 according to an implementation of the disclosed subject matter.

The at least one second sensor 106 may be communicatively coupled to the controller 114 shown in FIG. 4, and the controller 114 may control the drive system 108 so as to stop and/or move the mobile robot 100 before the light source 104 is within the predetermined distance of an object 113 (e.g., at least a portion of object 113a, 113b) based on at least a signal received from the at least one first sensor 102 and/or a signal received from the at least one second sensor 106. As shown in FIG. 1, the light source 104 may be disposed over the at least one second sensor 106. In some implementations, the at least one second sensor 106 may be oriented in a direction towards the light source 104. For example, the at least one first sensor 102 may be arranged so as to have a detection direction that is about parallel to a surface over which the mobile robot is travelling (e.g., the floor, ground, or the like) and/or towards the surface (e.g., a downward detection direction), and the at least one second sensor 106 may have a detection direction oriented upwards from the surface (e.g., in an upwards direction) towards the light source 104.

In some implementations, the at least one second sensor 106 may be a time-of-flight sensor, an ultrasonic sensor, a two-dimensional Light Detection and Ranging (LiDAR) sensor, a three-dimensional LiDAR sensor, and/or a radar (radio detection and ranging) sensor, or the like. The at least one second sensor 106 may have a field of view of 20-27 degrees. In some implementations, the at least one second sensor 106 may have a detection distance of 0.05-4 meters.

The mobile robot 100 may include a motor to drive the drive system 108 to move the mobile robot in an area, such as a room, a building, or the like. The drive system 108 may include wheels, which may be adjustable so that the drive system 108 may control the direction of the mobile robot 100.

In some implementations, the mobile robot 100 may include a base with the drive system 108, and at least one first sensor 102 may be disposed on the base. In this implementation, the at least one first sensor 102 may be a two-dimensional Light Detection and Ranging (LiDAR) sensor, a three-dimensional LiDAR sensor, three-dimensional cameras, or the like.

The controller 114 may control and/or operate the mobile robot 100 in an operation mode which may be a manual mode, an autonomous mode, and/or a tele-operation mode. In the manual mode, the controller 114 may receive on or more control signals from the user interface 110 and/or the stop button 112. For example, a user may control the movement, direction, and/or stop the motion of the mobile robot 100 by making one or more selections on the user interface 110. The stop button 112 may be an emergency stop (ESTOP) button which may stop all operations and/or movement of the mobile robot 100 when selected. In some implementations, the controller 114 may receive at least one control signal via a network interface 116 (shown in FIG. 4) when operating when operating in the tele-operation mode. For example, the network interface may receive control signals via network 130 from server 140, database 150, and/or remote platform 160, as described below in connection with FIG. 5.

In some implementations, the at least one first sensor 102 may be a time-of-flight sensor, a stereo vision sensor, a two-dimensional LiDAR sensor, a three-dimensional LiDAR sensor, or the like. For example, while the mobile robot 100 is moving in a direction, the at least one first sensor 102 may detect a geometry of one or more objects (e.g., object 113, having portions 113a and/or 113b) that may be in the path of the mobile robot 100. The output of the at least one first sensor 102 may be, for example, a point cloud of the one or more objects in the path of the mobile robot 100. In this example, there may be nothing (e.g., no objects) in the path of the mobile robot 100 up to the detection range of the at least one first sensor 102, which may be about 4 meters. When the at least one first sensor 102 may determine that one or more objects (e.g., object 113) are in the path of the mobile robot 100, the controller 114 may reduce an allowed maximum velocity of the mobile robot 100 for safety, so as to reduce and/or eliminate having the light source 104 impact the one or more objects which may damage the light source 104. For example, when the controller 114 is operating the mobile robot 100 in the autonomous mode, the controller 114 may determine whether the desired path (i.e., a planned path) may cause the mobile robot to impact the one or more objects (e.g., object 113). When the controller 114 is operating the mobile robot 100 in the manual or tele-operated modes, the controller 114 may receive a user command via the user interface 110, the stop button 112, and/or via the network interface 116. If the desired path may end with a collision, or may place the mobile robot 100 within a predetermined distance of an object which may cause a collision, the controller 114 may change the path of motion, or stop movement, of the mobile robot 100 by controlling the drive system 108.

When the at least one first sensor 102 is a stereo vision sensor, images from two sensors (i.e., where the two sensors may be part of the stereo vision sensor of the at least one first sensor 102) within a known distance from one another distance may be captured at a predetermined point in time, and/or at predetermined time intervals with a global shutter. The global shutter may be configured so that the two sensors of the stereo vision sensor may capture images about simultaneously. One or more features may be determined from the captured images, and be compared to one another to determine portions that are matching. As the focal length of the two sensors of the stereo vision sensor and the distance between the two sensors (e.g., about 6 cm) may be stored in memory 118 and/or fixed storage 120 (shown in FIG. 4), the controller 114 and/or the at least one first sensor 102 may use the captured images and the stored values to determine the distance from the at least one first sensor 102 to the object 113. In some implementations, the at least one sensor 102 may include at least one laser, LED, and/or OLED, to radiate one or more points on surfaces of objects, when the objects may be without identifying features (e.g., blank walls).

In some implementations, protection of the light source 104 may be increased by using the at least one second sensor 106 which may be disposed below the light source 104. The at least one second sensor 106 may be configured so that a detection path is towards the light source 104 (e.g., an upward path that may be at an angle from the surface over which the mobile robot 100 may travel). In some implementations, the at least one second sensor 106 may be disposed above the light source 104. In another implementation, the at least one second sensor 106 may include one sensor that is disposed above the light source 104, and another sensor that is disposed below the light source 104.

For example, the at least one second sensor 106 may be a time-of-flight (TOF) sensor. At least one photon of light may be output by the at least one second sensor 106, and may be transmitted through the air. When the at least one photon of light radiates the object 113, a portion of the light may be reflected by the object 113 may return to a receiver portion of the at least one second sensor 106. The at least one second sensor 106 may calculate the time between sending the at least one photon of light and receiving the reflection, and multiply this value by the speed of light in air, to determine the distance between the at least one second sensor 106 and the object 113. Typically, the calculated distance may be larger than the distance between the object 113 and the light source 104. The distance may differ from place to place, for example, because of different ceiling heights (e.g., which may reflect the one or more photons of light differently). When the determined distance is less than the distance to the location of the at least one second sensor, the controller 114 may stop the drive system 108 and/or change the direction of the mobile robot 100. This determination by the controller 114 may be based on the present direction of the mobile robot 100, the orientation of the mobile robot 100, the location of the at least one second sensor 106, and/or the physical dimension of the mobile robot 100. The at least one second sensor 106 may stop the mobile robot 100 by transmitting a signal to the controller 114 to change the path direction of the mobile robot 100 when operating in the autonomous mode. In another implementation, the at least one second sensor 106 may provide a control signal to the drive system 108 to stop the movement of the mobile robot 100.

FIG. 4 shows example components of the mobile robot 100 suitable for providing the implementations of the disclosed subject matter. The mobile robot 100 may include a bus 122 which interconnects major components of the mobile robot 100, such as the drive system 108, a network interface 116 operable to communicate with one or more remote devices via a suitable network connection, the controller 114, a memory 118 such as Random Access Memory (RAM), Read Only Memory (ROM), flash RAM, or the like, the stop button 112, the light source 104, the at least one first sensor 102, a user interface 110 that may include one or more controllers and associated user input devices such as a keyboard, touch screen, and the like, a fixed storage 120 such as a hard drive, flash storage, and the like, and the at least one second sensor 106.

The bus 122 allows data communication between the controller 114 and one or more memory components, which may include RAM, ROM, and other memory, as previously noted. Typically RAM is the main memory into which an operating system and application programs are loaded. A ROM or flash memory component can contain, among other code, the Basic Input-Output system (BIOS) which controls basic hardware operation such as the interaction with peripheral components. Applications resident with the mobile robot 100 are generally stored on and accessed via a computer readable medium (e.g., fixed storage 120), such as a solid state drive, hard disk drive, an optical drive, solid state drive, or other storage medium.

Figure 5:
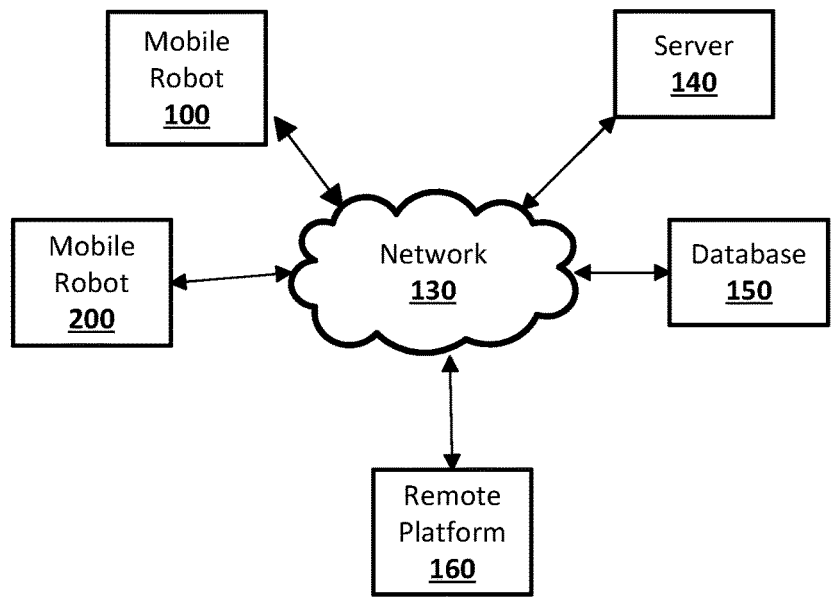
FIG. 5 shows a network configuration which may include a plurality of mobile robots according to implementations of the disclosed subject matter.

The network interface 116 may provide a direct connection to a remote server (e.g., server 140, database 150, and/or remote platform 160 shown in FIG. 5) via a wired or wireless connection (e.g., network 130 shown in FIG. 5). The network interface 116 may provide such connection using any suitable technique and protocol as will be readily understood by one of skill in the art, including digital cellular telephone, WiFi, Bluetooth(R), near-field, and the like. For example, the network interface 116 may allow the mobile robot 100 to communicate with other computers via one or more local, wide-area, or other communication networks, as described in further detail below. The mobile robot may transmit data via the network interface to the remote server that may include a path of operation, the surfaces and/or areas radiated with UV light, and the like.

Many other devices or components (not shown) may be connected in a similar manner. Conversely, all of the components shown in FIG. 4 need not be present to practice the present disclosure. The components can be interconnected in different ways from that shown. Code to implement the present disclosure can be stored in computer-readable storage media such as one or more of the memory 118, fixed storage 120, or on a remote storage location.

FIG. 5 shows an example network arrangement according to an implementation of the disclosed subject matter. Mobile robot 100 described above, and/or a similar mobile robot 200 may connect to other devices via network 130. The network 130 may be a local network, wide-area network, the Internet, or any other suitable communication network or networks, and may be implemented on any suitable platform including wired and/or wireless networks. The mobile robot 100 and/or mobile robot 200 may communicate with one another, and/or may communicate with one or more remote devices, such as server 140, database 150, and/or remote platform 160. The remote devices may be directly accessible by the mobile robot 100, 200 or one or more other devices may provide intermediary access such as where a server 140 provides access to resources stored in a database 150. The mobile robot 100, 200 may access remote platform 160 or services provided by remote platform 160 such as cloud computing arrangements and services. The remote platform 160 may include one or more servers 140 and/or databases 150.

More generally, various implementations of the presently disclosed subject matter may include or be embodied in the form of computer-implemented processes and apparatuses for practicing those processes. Implementations also may be embodied in the form of a computer program product having computer program code containing instructions embodied in non-transitory and/or tangible media, such as solid state drives, DVDs, CD-ROMs, hard drives, USB (universal serial bus) drives, or any other machine readable storage medium, such that when the computer program code is loaded into and executed by a computer, the computer becomes an apparatus for practicing implementations of the disclosed subject matter. Implementations also may be embodied in the form of computer program code, for example, whether stored in a storage medium, loaded into and/or executed by a computer, or transmitted over some transmission medium, such as over electrical wiring or cabling, through fiber optics, or via electromagnetic radiation, such that when the computer program code is loaded into and executed by a computer, the computer becomes an apparatus for practicing implementations of the disclosed subject matter. When implemented on a general-purpose microprocessor, the computer program code segments configure the microprocessor to create specific logic circuits.

In some configurations, a set of computer-readable instructions stored on a computer-readable storage medium may be implemented by a general-purpose processor, which may transform the general-purpose processor or a device containing the general-purpose processor into a specialpurpose device configured to implement or carry out the instructions. Implementations may include using hardware that has a processor, such as a general purpose microprocessor and/or an Application Specific Integrated Circuit (ASIC) that embodies all or part of the techniques according to implementations of the disclosed subject matter in hardware and/or firmware. The processor may be coupled to memory, such as RAM, ROM, flash memory, a hard disk or any other device capable of storing electronic information. The memory may store instructions adapted to be executed by the processor to perform the techniques according to implementations of the disclosed subject matter.

The foregoing description, for purpose of explanation, has been described with reference to specific implementations. However, the illustrative discussions above are not intended to be exhaustive or to limit implementations of the disclosed subject matter to the precise forms disclosed. Many modifications and variations are possible in view of the above teachings. The implementations were chosen and described in order to explain the principles of implementations of the disclosed subject matter and their practical applications, to thereby enable others skilled in the art to utilize those implementations as well as various implementations with various modifications as may be suited to the particular use contemplated.

The invention claimed is:

1. A device comprising:
a mobile robot including:
 a base that includes a motor and a drive system, where the motor is configured to drive the drive system to move the mobile robot in an area;
 a light source to output ultraviolet light disposed over the base, the light source having a first side and a second side;
 at least one first sensor to detect a geometry of an object and determine that the object will impact the light source based on the detected geometry of the object and a path of movement of the mobile robot in the area and output a signal based on the determination; and
 a controller, communicatively coupled to the drive system, the light source, and the at least one first sensor to control the drive system to stop or change the path of the mobile robot before the light source impacts the object based on at least the signal received from the at least one first sensor.

2. The device of claim 1, wherein the at least one first sensor has a field of view of 70 degrees diagonally.

3. The device of claim 1, wherein the at least one first sensor has a detection distance of 0.2-4 meters.

4. The device of claim 1, wherein the at least one first sensor comprises a first side sensor disposed on a first side of the device and the second side sensor is disposed on a second side of the device.

5. The device of claim 4, wherein the first side sensor and the second side sensor are disposed over the light source.

6. The device of claim 1, further comprising:
at least one second sensor that is communicatively coupled to the controller,
wherein the controller controls the drive system so as to stop or move the mobile robot before the light source is within the predetermined distance of the object based on at least one selected from a group consisting of: the signal received from the at least one first sensor and a signal received from the at least one second sensor.

7. The device of claim 6, wherein the light source is disposed over the at least one second sensor.

8. The device of claim 7, wherein the at least one second sensor is oriented in a direction towards the light source.

9. The device of claim 6, wherein the at least one second sensor is selected from a group consisting of: a time-of-flight sensor, an ultrasonic sensor, a two-dimensional Light Detection and Ranging (LiDAR) sensor, a three-dimensional LiDAR sensor, and a radar sensor.

10. The device of claim 6, wherein the at least one second sensor has a field of view of 20-27 degrees.

11. The device of claim 6, wherein the at least one second sensor has a detection distance of 0.05-4 meters.

12. The device of claim 1, wherein the mobile robot includes a base with the drive system, and the at least one first sensor is selected from a group consisting of: a two-dimensional Light Detection and Ranging (LiDAR) sensor, a three-dimensional LiDAR sensor, and three-dimensional cameras,
wherein the at least one first sensor is disposed on the base.

13. The device of claim 1, wherein the controller operates the mobile robot in an operation mode selected from at least one of the group consisting of: a manual mode, an autonomous mode, and a tele-operation mode.

14. The device of claim 13, wherein the controller receives at least one control signal from a user interface when operating in the manual mode, or from a communications interface when operating in the tele-operation mode,
wherein the user interface and the communications interface are communicatively coupled to the controller.

* * * * *